United States Patent
Murphy

(10) Patent No.: US 7,494,243 B2
(45) Date of Patent: Feb. 24, 2009

(54) MULTI-COLOR ILLUMINATION DISPLAY APPARATUS

(75) Inventor: Mason E. Murphy, Franklin, TN (US)

(73) Assignee: Whitegate Partners, LLC, Franklin, TN (US)

(*) Notice: Subject to any disclaimer, the term of this patent is extended or adjusted under 35 U.S.C. 154(b) by 861 days.

(21) Appl. No.: 10/298,223

(22) Filed: Nov. 18, 2002

(65) Prior Publication Data

US 2004/0095746 A1    May 20, 2004

(51) Int. Cl.
*F21V 9/10* (2006.01)

(52) U.S. Cl. ............... 362/231; 362/236; 362/240; 362/248; 362/310; 362/311

(58) Field of Classification Search ......... 362/559, 362/560, 565, 85, 86, 87, 227, 230, 231, 362/235, 236, 237, 240, 248, 276, 290, 291, 362/292, 310, 311, 362, 372, 367, 800, 806, 362/802; 315/76; 359/443, 444, 449, 460; 446/175, 219, 485; 40/444, 431

See application file for complete search history.

(56) References Cited

U.S. PATENT DOCUMENTS

| | | | | |
|---|---|---|---|---|
| 1,790,903 A * | 2/1931 | Craig | ...................... | 315/76 |
| 1,792,731 A * | 2/1931 | Craig | ...................... | 40/433 |
| 1,846,533 A * | 2/1932 | Thompson | ...................... | 40/361 |
| 2,070,088 A * | 2/1937 | Montaruli | ...................... | 362/86 |
| 2,090,086 A * | 8/1937 | Weiner | ...................... | 362/205 |
| 2,170,368 A * | 8/1939 | Gentilini | ...................... | 40/433 |
| 3,228,278 A * | 1/1966 | Wortman | ...................... | 84/464 R |
| 3,366,786 A * | 1/1968 | Delano | ...................... | 40/433 |
| 3,401,596 A * | 9/1968 | Hirsch | ...................... | 362/310 |
| 3,540,343 A * | 11/1970 | Rifkin | ...................... | 84/464 R |
| 3,568,357 A * | 3/1971 | Lebensfeld | ...................... | 446/91 |
| 3,603,195 A * | 9/1971 | Williams | ...................... | 40/433 |
| 3,609,339 A * | 9/1971 | Smith | ...................... | 362/293 |
| 3,611,069 A * | 10/1971 | Galginaitis et al. | ...................... | 257/90 |
| 3,700,880 A * | 10/1972 | Smith | ...................... | 40/433 |
| 3,875,456 A * | 4/1975 | Kano et al. | ...................... | 257/89 |
| 4,176,581 A * | 12/1979 | Stuyvenberg | ...................... | 362/232 |
| 4,276,705 A * | 7/1981 | Barth et al. | ...................... | 40/579 |
| 4,307,528 A * | 12/1981 | Dewees et al. | ...................... | 40/431 |
| 4,809,584 A * | 3/1989 | Forrest | ...................... | 84/464 R |
| 4,835,661 A * | 5/1989 | Fogelberg et al. | ...................... | 362/223 |
| 4,875,143 A * | 10/1989 | Fernandez | ...................... | 362/86 |
| 4,953,220 A * | 8/1990 | Murayama et al. | ...................... | 381/86 |
| 4,992,704 A * | 2/1991 | Stinson | ...................... | 315/312 |
| 5,233,375 A * | 8/1993 | Williams et al. | ...................... | 352/43 |
| 5,367,349 A * | 11/1994 | Zeiler | ...................... | 362/202 |
| 5,391,105 A * | 2/1995 | Jones | ...................... | 446/485 |

(Continued)

*Primary Examiner*—Ismael Negron
(74) *Attorney, Agent, or Firm*—Banner & Witcoff, Ltd.

(57) ABSTRACT

An illumination apparatus configured to generate multi-color light and that may be operated in a variety of visual modes. The illumination apparatus may have, e.g., a housing having a display surface, first and second multi-color light sources directing light onto the display surface, and a perforated shield coupled to the housing. At least a portion of the light from each of the first and second multi-color light sources may be reflected from the display surface and pass through the shield. The illumination apparatus may further include one or more speakers that may operate in a variety of audio modes. The illumination apparatus may further produce full-spectrum white light.

18 Claims, 5 Drawing Sheets

U.S. PATENT DOCUMENTS

| | | | |
|---|---|---|---|
| 5,461,188 A * | 10/1995 | Drago et al. | 362/103 |
| 5,471,371 A * | 11/1995 | Koppolu et al. | 362/307 |
| 5,644,860 A * | 7/1997 | Piper et al. | 40/579 |
| 6,000,493 A * | 12/1999 | Chen | 362/86 |
| 6,011,650 A * | 1/2000 | Parker et al. | 359/567 |
| 6,150,774 A * | 11/2000 | Mueller et al. | 315/291 |
| 6,164,792 A * | 12/2000 | Nakagome | 362/86 |
| 6,166,496 A * | 12/2000 | Lys et al. | 315/316 |
| 6,179,449 B1 * | 1/2001 | Chen | 362/230 |
| 6,447,138 B1 * | 9/2002 | Yang | 362/96 |
| 6,545,418 B1 * | 4/2003 | Kolpasky et al. | 362/86 |
| 6,623,124 B2 * | 9/2003 | Okura | 353/43 |
| 6,746,131 B1 * | 6/2004 | Goldstein et al. | 362/96 |

* cited by examiner

MULTI-COLOR ILLUMINATION DISPLAY APPARATUS

FIELD OF THE INVENTION

The present invention is directed generally to an illumination apparatus, and more particularly to an illumination apparatus that is capable of generating multiple colors of light.

BACKGROUND OF THE INVENTION

Sources of light, beginning with the flame and then the incandescent bulb, have been used for centuries to aid the human eye in an otherwise dark environment. More recently, light sources have been used for a variety of other purposes, such as for achieving a decorative effect or for treating light deficiency disorders. Indeed, there has recently been a substantial growth in demand for light sources to achieve such functions.

SUMMARY OF THE INVENTION

Aspects of the present invention are directed to an illumination apparatus that is configured to generate multi-color light in a pleasing fashion and that may be operated in a variety of visual modes. The illumination apparatus may be made to be attractive and decorative in appearance. Different finishes may be applied to match a user's desired décor. One may even desire to use the illumination apparatus much the way that candles, fish tanks, wave tanks, or even lava lamps have been used. People generally have enjoyed the presence of each of these items because of the personality, motion, and mood they add to a room.

According to further aspects of the present invention, the illumination apparatus may have one or more multi-color light sources configured to change colors over time. The multi-color light sources may be directed onto a reflective surface or panel to produce additional effects.

The illumination apparatus may further include one or more speakers for producing sound in combination with or independently from the generated multi-color light. Thus, the illumination apparatus may be used for both audio and visual entertainment. The audio may also operate in a variety of audio modes. The illumination apparatus may thus be coupled with an audio source such as a compact disc player or a computer to produce music or other audio. For instance, an MP3 file or compact disc may be played by a computer through the illumination apparatus, and the multi-color lights may change color, change intensity, and "dance" to the music. Accordingly, the user may use a software program on a computer coupled to the illumination apparatus, and the illumination apparatus would provide a personal light show in accordance with instructions from the software. The computer may be coupled to the illumination apparatus by, e.g., a universal serial bus (USB) connection using an RS-232 data protocol. RS-232 based code, or code in another format, may be encoded in music, gaming software, learning software, and/or any other application or other software. For example, where the music is encoded with instructions, flags, or other relevant coding, the illumination apparatus may provide lighting while the music is playing in response to the coding associated with the music.

According to further aspects of the present invention, the illumination apparatus may be configured to generate light, such as full-spectrum light, that is suitable for treating light deficiency disorders and/or for reducing eyestrain.

According to still further aspects of the present invention, the illumination apparatus may be configured to couple with a display such as to the sides of a computer display. Such a configuration may make the computer experience more enjoyable to a user.

Further aspects of the invention are directed to providing one or more interchangeable filters to be used with the illumination apparatus. A plurality of such filters may be provided in combination with an illumination apparatus, such as in a kit form. The filters may be changed by the user depending upon the user's mood and/or the desired functionality of the illumination apparatus.

These and other features of the invention will be apparent upon consideration of the following detailed description of preferred embodiments.

BRIEF DESCRIPTION OF THE DRAWINGS

The foregoing summary of the invention, as well as the following detailed description of preferred embodiments, is better understood when read in conjunction with the accompanying drawings, which are included by way of example, and not by way of limitation with regard to the claimed invention.

DETAILED DESCRIPTION OF ILLUSTRATIVE EMBODIMENTS

Figures 1, 2:
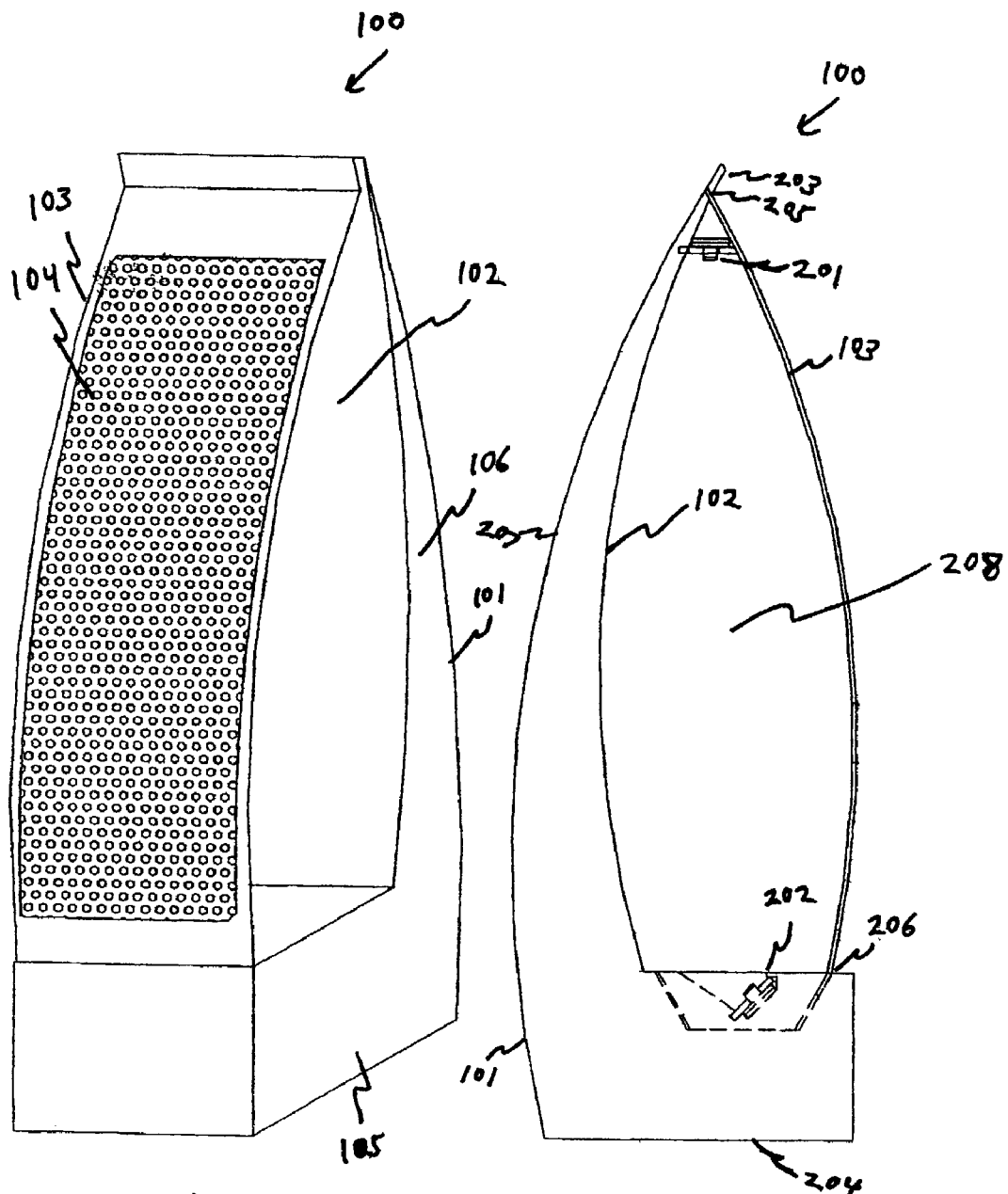
FIG. 1 is a perspective front view of an illustrative embodiment of an illumination apparatus in accordance with at least one aspect of the present invention.
FIG. 2 is a side view of the illumination apparatus of FIG. 1.

Referring to FIG. 1, an illustrative embodiment of an apparatus for producing multi-color illumination (also called herein an "illumination apparatus") 100 may include a main body/housing 101, a display surface 102 of the main body 101, and/or a filter 103. Although the main body 101 may be of any shape desired, the main body 101 is shown in FIG. 1 as having a bottom base portion 105 and an elongated back portion 106, or vertical extension, extending from the base portion 105. The elongated back portion 106 may taper as it extends away from the base portion 105. However, the particular shape of the main body 101 is an ornamental consideration and is not important to the present invention. The main body 101 may be made of any material, such as plastic, metal, or wood, and/or any combination of materials. The display surface 102 of the main body 101 may be flat, curved (as in FIG. 1), concave, convex, or any other shape, and may be partially or fully reflective. In the illustrated embodiment of FIG. 1, the display surface 102 is concave. To make the display surface 102 reflective, it may be comprised of a reflective material and/or be painted or otherwise coated with a reflective coating, such as metallic paint. The filter 103 may be permanently or removeably coupled with the main body 101, and may include one or more perforations 104, such that light may pass through the perforations 104. The filter 103 may partially shield the light reflected from the display surface 102 from the point of view of a user standing in front of the illumination apparatus 100. The area formed between the main body 101 and the filter 103 may be unenclosed (ie., not fully enclosed).

Referring to the side view of FIG. 2, the display surface 102 and the filter 103 (when mounted on the main body 101) may be opposed facing concave surfaces. The main body 101 may further include a rear surface 207 substantially opposite from the display surface 102. The illumination apparatus 100, when the filter 103 is attached, may include one or more (and in the illustrated embodiment, two) sides 208 that are substantially open, thus forming an unenclosed volume between the display surface 102 and the filter 103.

The filter 103 may be mounted into grooves 205, 206 in the main body 101. When mounted on the main body 101, a user may slightly flex the filter 103 such that the filter 103 is under tension and pressed against the walls of the grooves 205, 206, thereby preventing the filter 103 from slipping out of the grooves 205, 206.

The illumination apparatus 100 may include one or more multi-color light sources 201, 202. A multi-color light source is any light source that is configured to change colors over time. The multi-color light sources 201, 202, may include one or more light-emitting diodes (LEDs), organic light-emitting diodes (OLEDs), incandescent light sources, luminescent light sources, fluorescent light sources, plasma light sources, lasers, and/or any other type of light source. The arrangement for changing the color emitted from the multi-color light sources 201, 202 may be by the use of various filters, reflectors, combinations of light colors from multiple sub-sources of light, and/or any other arrangement. The light emitted from the multi-color light sources 201, 202 may be diffuse, direct, indirect, coherent, incoherent, or any other type of light. The multi-color light sources 201, 202 may over time change color smoothly over a frequency range and/or jump in increments of frequency, and may further change in intensity over time. Multi-color light sources per se are known, such as the multicolored LEDs disclosed in U.S. Pat. No. 6,016,038 to Mueller et al., hereby incorporated by reference as to its entirety.

The multi-color light sources 201, 202 may be disposed anywhere along the main body 101 as desired. In the illustrative embodiment of FIG. 2, the multi-color light source 201 is disposed near one end 203 of the main body 101 and the other multicolor light source 202 is disposed near the other opposite end 204 of the main body 101. Each of the multi-color light sources 201, 202 may be at least partially directed, or aimed, toward the display surface 102. The light from the multi-color light sources 201, 202 may be cast on to the display surface 102 and at least partially reflected off of the display surface 102. As shown in FIG. 2, the multi-color light sources 201, 202 may be directed in different, or even opposite, directions, and yet still be at least partially directed toward the display surface 102.

Figure 3:
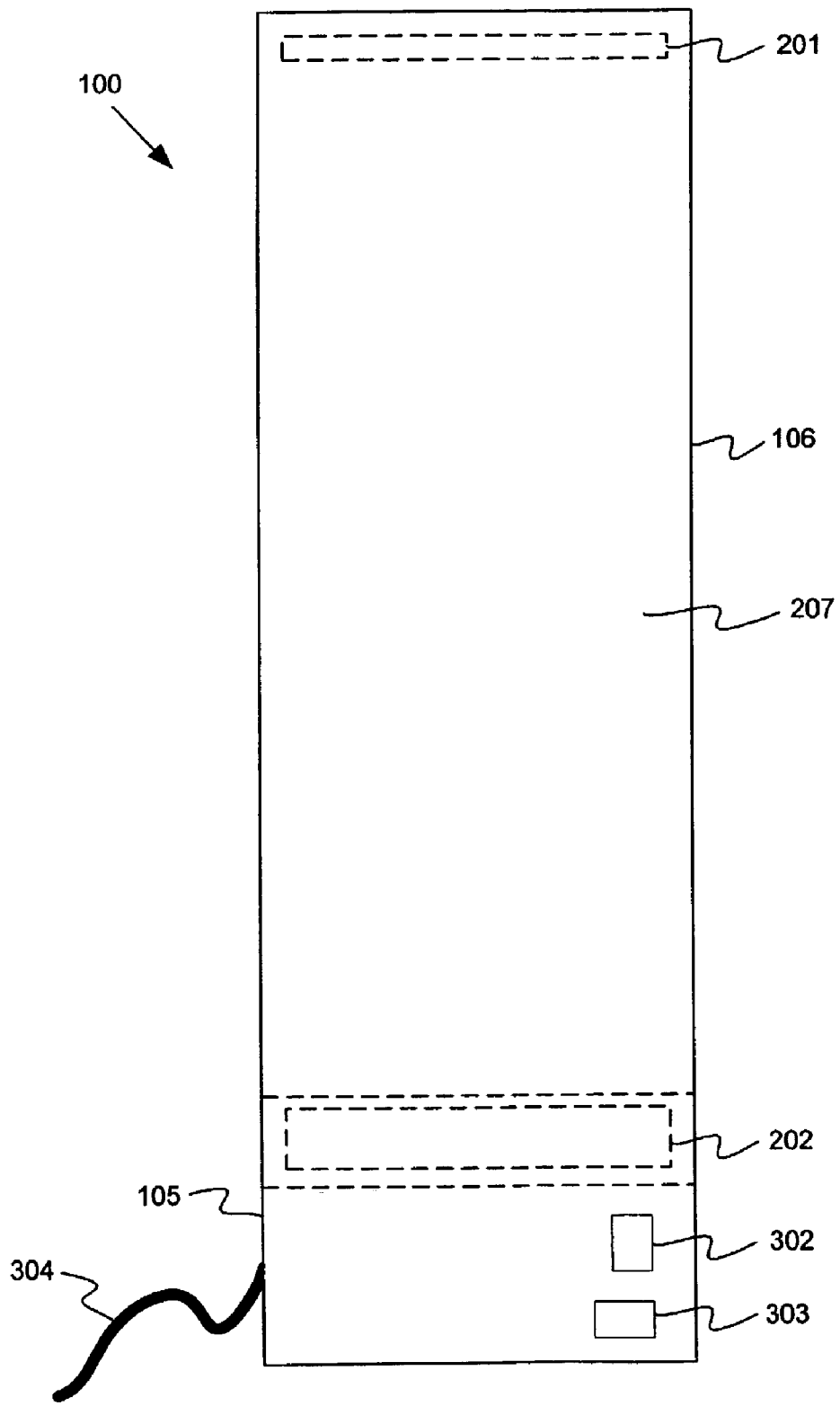
FIG. 3 is a rear view of the illumination apparatus of FIG. 1.

Referring to FIG. 3, the illumination apparatus 100 may include one or more receptacles 301 for receiving power, and/or one or more user control interfaces, such as switches 302, 303, for controlling the operation of the illumination apparatus 100. One or more cables 304 for communicating with an external controller 703 (FIG. 7) may also be supplied to control the operation of the illumination apparatus 100.

The cables 304 may include, e.g., a universal serial bus (USB) cable that may be used to control and/or power the illumination apparatus 100. Alternatively, the illumination apparatus 100 may include a wireless receiver and/or transmitter for communicating with the external controller.

Figure 4:
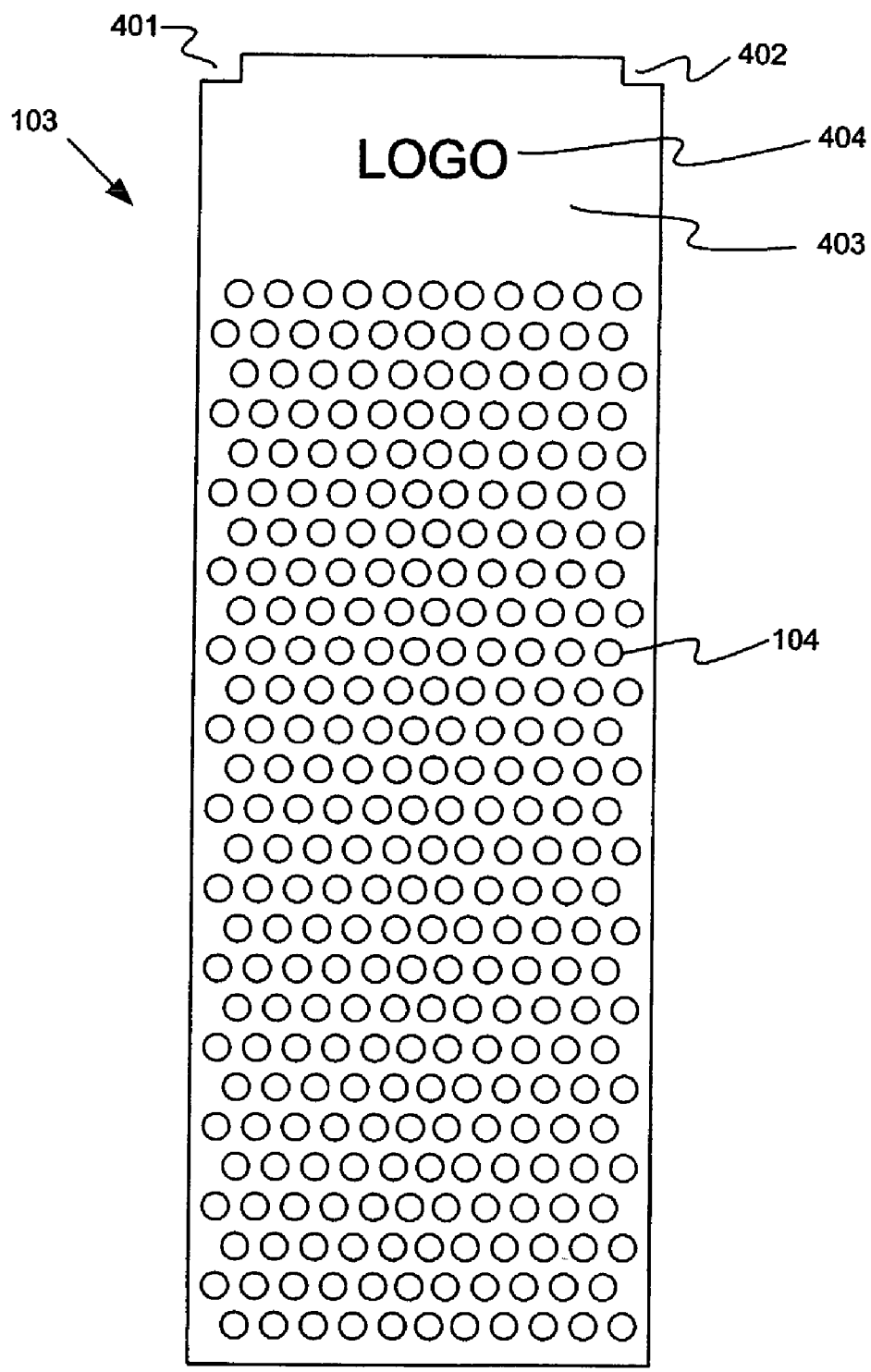
FIG. 4 is a front view of an illustrative embodiment of a filter, in accordance with at least one aspect of the present invention, that is disassembled from the illumination apparatus housing.

Referring to FIG. 4, as previously discussed, the filter 103 may include one or more perforations 104. The perforations 104 may each be of any shape, such as circular, rectangular, oval, or any other geometric or non-geometric shape. In one illustrative embodiment, the perforations may be circular and approximately $\frac{1}{16}$ to $\frac{1}{4}$ inch in diameter and spaced apart from each other by approximately $\frac{1}{32}$ to $\frac{1}{4}$ inch. Also, in the illustrative embodiment, the filter may be approximately $\frac{1}{32}$ to $\frac{1}{8}$ inch thick by approximately 3 to 4 inches wide by approximately 10 to 14 inches tall. However, any dimensions may be used. The perforations 104 may be arranged on the filter 103 as one or more rows and/or columns, or arranged in any other manner. For example, the perforations 104 may further be formed, collectively or individually, in the shape of one or more indicia, such as symbols, pictures, text, icons, trademarks, service marks, and/or the like.

The filter 103 may be made of any material, such as plastic, metal, or wood, and/or any combination of materials, and may be partially or fully transparent, translucent, partially translucent, or opaque based on its light transmittance. The filter 103 may be flexible or inflexible. Where the filter 103 is not opaque, light may pass not only through the perforations 104 but also through the material of the filter 103 itself. The filter 104 may further include one or more notches 401, 402 that allow the filter 104 to more securely couple with the main body 101. The filter 104 may further have one or more areas 403 in which there are no perforations, such as an area of approximately 1 to 3 square inches, suitable for allowing indicia 404 such as text or graphics to be printed thereon. Such indicia may include, for example, a logo, trademark or service mark.

Figure 5:
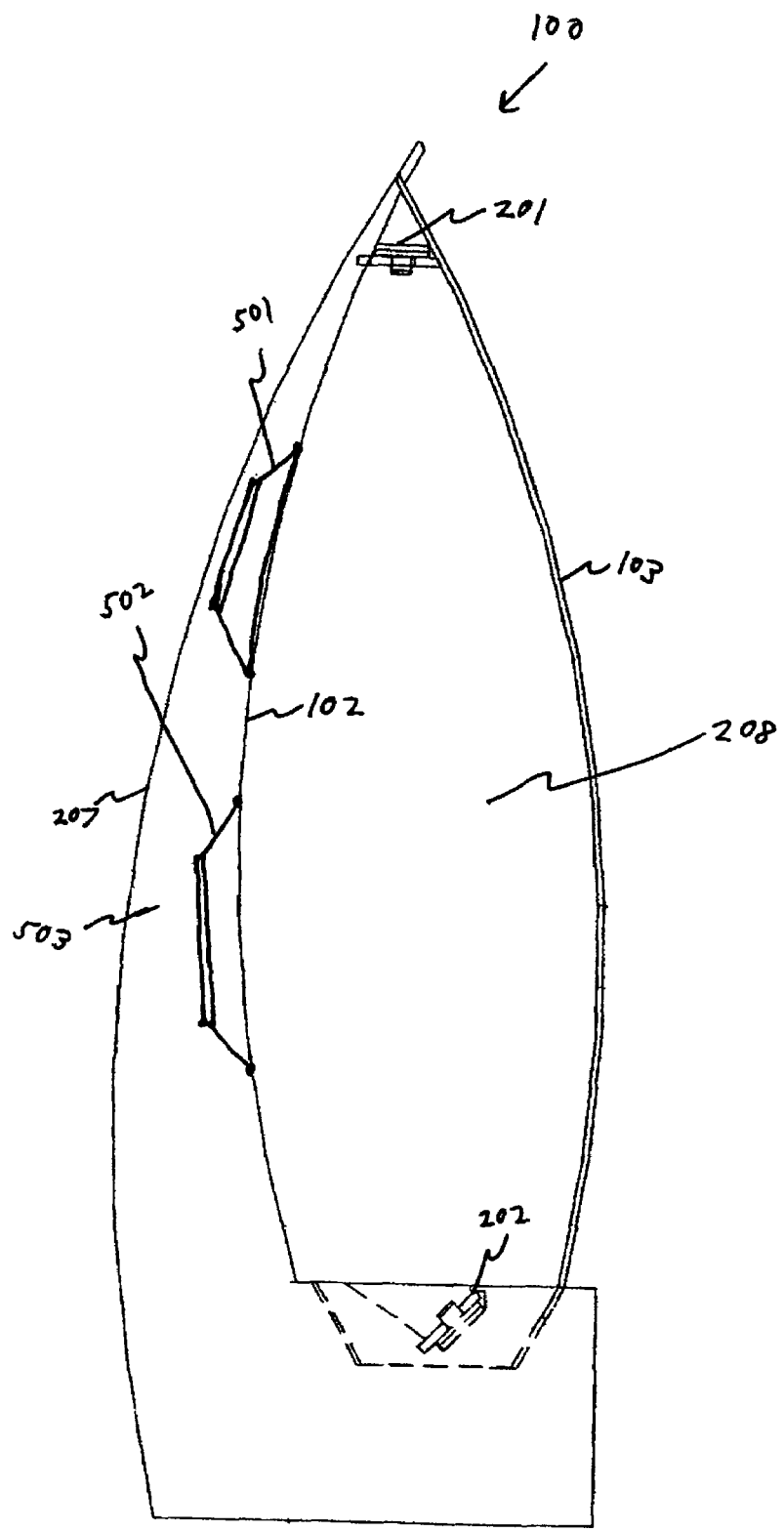
FIG. 5 is a side view of the illumination apparatus of FIG. 1 having an illustrative speaker in accordance with at least one aspect of the present invention.

Referring to FIG. 5, the illumination apparatus 100 may further include one or more speakers 501, 502 disposed partially or fully behind the display surface 102 and directed toward the surface. Thus, the display surface 102 may be considered to be one side of a dividing wall that divides a rear portion of the illumination apparatus 100 containing the speakers 501, 502 from a front portion of the illumination apparatus 100. The speakers 501, 502 may be attached directly or indirectly to the wall. The display surface 102 may thus both allow sound to pass through from the rear portion and also reflect light directed from the front portion. The speakers 501, 502 may be any type of sound-generating element, such as a magnetically driven acoustical speaker commonly used in household audio systems, a piezoelectric element, a subwoofer, or an electrostatic speaker. In some embodiments, the speakers 501, 502 may include approximately 1-inch micro-drivers. The speakers 501, 502 may be single-way or multi-way speakers. In those embodiments having one or more speakers, it may be advantageous for the display surface 102 to be perforated to allow sound to more easily pass through the perforations. Alternatively, the display surface 102 may be made of cloth, mesh, screen, or other similar material that reduces the attenuation and distortion of sound passing through the material. Also, the speakers 501, 502 may be partially or fully enclosed in a cavity 503 formed by the main body 101, in particular the display surface 102 and the rear surface 207. The cavity may be designed to optimize the acoustical output of the illumination apparatus 100.

As will be discussed in more detail below, the speakers may be used to produce sound based on audio signals input to the illumination apparatus 100, based on control signals input to the illumination apparatus 100, and/or based on acoustical information stored by the illumination apparatus 100 itself. Also as further discussed below, one or more of the multi-color light sources 201, 202 may be controlled in synchronicity with one or more of the speakers 501, 502 to achieve a variety of audio-visual effects.

Figure 6:
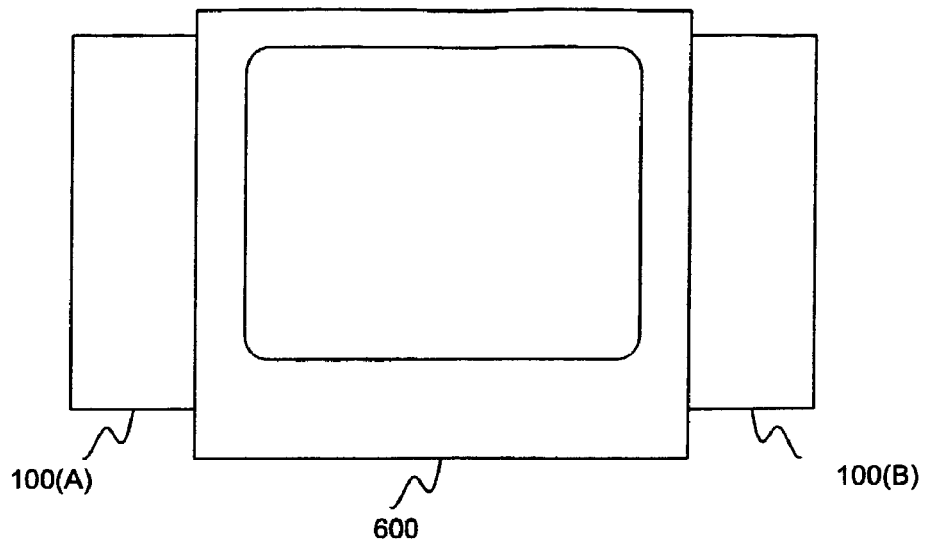
FIG. 6 is a front view of two illustrative illumination apparatuses, coupled with a video display device in accordance with at least one aspect of the present invention.

One or more of the illumination apparatus 100 may be mounted to a display device such as a computer monitor or television. FIG. 6 shows illumination apparatuses 100(A), 100(B) mounted to a display device 600. The illumination apparatuses may be permanently or removeably mounted, such as by a clip, VELCRO (e.g., hook and loop fastener arrangement), screws, magnets, or any other suitable mechanical hardware arrangement. Alternatively, the one or more illumination devices may be bodily incorporated as part of the display device 600. Where the illumination devices 100(A), 100(B) include speakers, it may be particularly desirable to mount them on the left and right sides of the display device 600, such that the speaker of the left illumination device 100(A) plays the left track of an audio signal and the speaker of the right illumination device 100(B) plays the right track of the audio signal. More than two illumination devices, each with speakers, may also be used together to produce surround sound effects when controlled by a surround-sound audio source. In addition, a subwoofer unit to control bass sound may be used for better acoustical performance.

Figure 7:
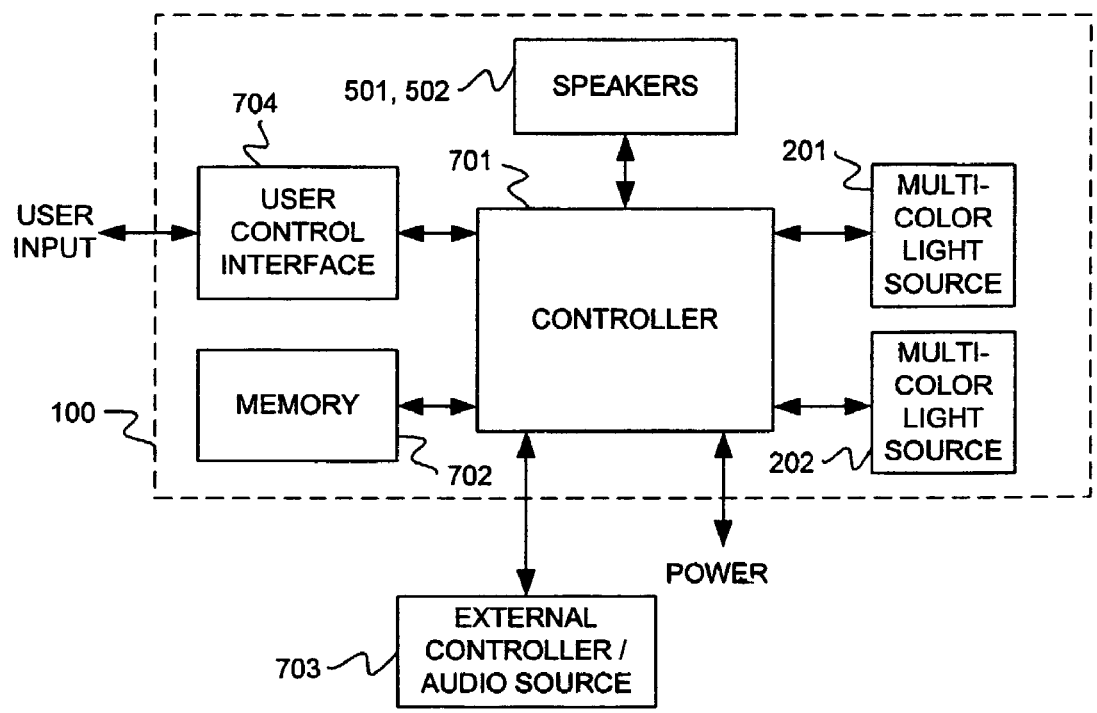
FIG. 7 is an illustrative functional block diagram of an illumination apparatus in accordance with at least one aspect of the present invention.

An illustrative functional description of the illumination apparatus 100 is now provided with reference to FIG. 7. The illumination apparatus 100 may include a controller 701, which may be one or more processors (such as a microprocessor), hardwired circuits, and/or the like. The controller 701 may further include one or more interfaces and/or drivers for communicating with other elements of the illumination apparatus 100. The controller 701 may be coupled to one or more of the speakers 501, 502, multi-color light sources 201, 202, and/or a user control interface 704. The controller 701 may further be coupled to a memory 702, and external controller and/or audio source 703, and/or a power source. The power source may be external to or part of the illumination apparatus 100, and where the power source is part of the illumination apparatus 100 it may include a battery. The external controller and/or audio source 703 may be coupled to the illumination apparatus 100 in a variety of ways, such as by a USB connection that provides both an RS-232 data stream and power to the illumination apparatus 100. Although the various functional blocks of FIG. 7 are shown as separate blocks, some or all of the individual functional blocks may be physically combined or separate physical elements as desired. In addition, portions of some or all of the functional blocks may be physically subdivided. For example, one or both of the multi-color light sources 201, 202 may physically incorporate at least a portion of the controller 701, such as on a single semiconductor chip and/or circuit board substrate.

The controller 701 may control one or more modes in which the illumination apparatus 100 operates. The modes may include visual modes and/or audio modes. The controller 701 may control the modes based on hard-wired circuitry and/or based on software instructions stored in the memory 702. Visual modes may affect how one or more of the multi-color light sources 201, 202 operate. For example, depending upon the selected visual mode, the controller 701 may cause one or more of the multi-color light sources 201, 202 to flash, strobe, change colors smoothly over time, maintain a single color, fading in and out in intensity, or any combination or subcombination thereof. The visual mode may also affect the speed and/or intensity at which the multi-color light sources 201, 202 operate, as well as whether the various multi-color light sources 201, 202 are synchronized with each other or run independently from each other.

Similarly, audio modes may affect how one or more of the speakers 501, 502 operate. For instance, depending upon the selected audio mode, one or more of the speakers 501, 502 may produce sound based on an external audio source and/or an internal audio source, as well as whether the speakers 501, 502 operate in synchronization with the operation of the multi-color light sources 201, 202 or independently from them. The user control interface 704, which may comprise one or more of the switches 302, 303, may be used by the user of the illumination apparatus 100 to select audio and/or visual modes.

The external audio source and/or controller 703 may include one or more home audio components such as a compact disc player, a radio, a personal computer, an amplifier, and/or the like. The external audio source and/or controller 703 may further provide one or more control signals to affect one or more audio and/or visual modes of the illumination apparatus 100. For example, a personal computer may provide an audio signal such as music as well as an RS-232 control signal that commands the controller 701 to operate in a particular audio and/or visual mode. The control signal may further include timing signals to indicate to the controller 701 when to perform a particular action in the selected mode, such as when to flash the multi-color light sources 201, 202 and/or when to display particular colors.

The controller 701 may, depending upon the audio mode, cause one or more of the speakers 501, 502 to produce sound based upon an internal audio source that is part of the illumination apparatus 100, such as disposed within and/or on the housing of the main body 101. The internal audio source may include a compact disc player, a radio, a personal computer, an amplifier, and/or the like. The internal audio source may further include the memory 702 and/or any other type of storage device such as a replaceable memory card. The memory 702 or other storage device may include data representing prerecorded audio information and/or instructions for generating audio. For example, the memory 702 may store digitized audio information that may be converted by the controller 701 to analog form and played by the speakers 501, 502. In this regard, the controller 701 may include one or more digital-to-analog converters (not explicitly shown). The digital-to-analog converters may further convert digital audio information from the external audio source 703 into analog audio information. The stored data may represent audio information in many forms, such as music, speech, sound effects, or a simulated nature environment such as ocean waves breaking, a gurgling stream, or blowing wind. In addition, where soothing sounds or other data stored in the memory 702 (or memory card) are played over the speakers 501, 502, the multi-color light sources 201, 202 may operate in synchronization with the audio, such as by changing colors to reflect the moods of various portions of the audio.

One or more of the multi-color light sources 201, 202 may further be configured to output light (such as white full-spectrum light) with frequency components suitable for relieving light deficiency disorders such as seasonal affective disorder (SAD), depression, circadian rhythm disorders, and/or the like. Such light sources per se are known, such as various products offered by The SunBox Company, http://www.sunbox.com. The multi-color light sources 201, 202 may further produce light suitable for reducing eyestrain, especially where the illumination apparatus 100 is utilized in combination with a computer display. In alternative embodiments, the light produced for relieving light deficiency disorders and/or for reducing eyestrain may be a non-multi-color light source (i.e., a light source that maintains a substantially constant frequency spectrum output) different from the multi-color light sources 201, 202.

An illumination apparatus in accordance with aspects of the present invention, such as the illumination apparatus 100, may be sold or otherwise marketed in combination with (such as in the form of a kit) a plurality of interchangeable filters such as the filter 103. The kit may include two, three, four, or more interchangeable filters. Each of the plurality of filters in the kit may have properties that differ from one another. For example, each of the filters may have a different arrangement and/or style of perforations, be of a different color, have a different transmittance of light, have one or more other different optical properties, and/or be of a different material. Thus, a user obtaining such a kit may be able to attach a different one of the filters to the illumination apparatus as desired. The kit may further a pair of illumination apparatuses, especially where the illumination apparatuses each include a speaker. The kit may further include a personal computer and/or computer display, especially where the illumination apparatuses are configured to mount to the computer display.

While exemplary systems and methods as described herein embodying various aspects of the present invention are shown by way of example, it will be understood, of course, that the invention is not limited to these embodiments. Modifications may be made by those skilled in the art, particularly in light of the foregoing teachings. For example, each of the elements of the aforementioned embodiments may be utilized alone or in combination with elements of the other embodiments. Also, the invention has been defined using the appended claims, however these claims are exemplary in that the invention is intended to include the elements and steps described herein in any combination or sub combination. It will also be appreciated and understood that modifications may be made without departing from the true spirit and scope of the invention.

What is claimed is:

1. An apparatus for producing multi-color illumination, comprising:
    a housing including an elongated and curved display surface fixed relative to the housing;
    a first multi-color light source coupled to and disposed near a first end of the apparatus and directed onto the display surface;
    a second multi-color light source coupled to and disposed near a second end of the apparatus opposite the first end and directed onto the display surface; and
    a shield coupled to the housing, the shield and the display surface forming an unenclosed volume having at least two open sides.

2. A kit comprising:
    a multi-color illumination apparatus; and
    a plurality of elongated flexible interchangeable filters, the filters each being removeably attachable to the illumination by flexing the filter into a curve to produce tension in the filter such that the filter is attached to the illumination apparatus while under the tension, each filter having different optical qualities.

3. The kit of claim 2, wherein each of the plurality of filters has a different arrangement of a plurality of perforations.

4. The kit of claim 2, wherein each of the plurality of filters has a different light transmittance.

5. The kit of claim 2, further including a display device.

6. The apparatus of claim 2, wherein when each of the filters is coupled to the multi-color illumination apparatus, the respective filter is positioned so as to at least partially shield multi-color light emitted by the multi-color illumination apparatus.

7. An apparatus for producing multi-color illumination, comprising:
    a housing having a display surface fixed relative to the housing;
    a first multi-color light source directing light in a first direction onto the display surface;
    a second multi-color light source directing light in a second different direction onto the display surface; and
    a perforated shield coupled to the housing, at least a portion of the light from each of the first and second multi-color light sources being reflected from the display surface and passing through the shield.

8. The apparatus of claim 7, wherein the shield is removeably attachable to the housing.

9. The apparatus of claim 7, wherein the first and second multi-color light sources each comprise at least one light-emitting diode.

10. The apparatus of claim 7, wherein the display surface is elongated and has a central portion and opposing end portions, and wherein the display surface is concave such that the central portion of the display surface is farther from the shield than the end portions of the display surface.

11. The apparatus of claim 10, wherein the shield when attached to the housing forms an opposing concave surface facing the display surface.

12. An apparatus for producing multi-color illumination, comprising:
    a base portion including a first multi-color light source;
    a vertical extension coupled to the base portion and including a light-reflecting surface fixed relative to the base portion and the vertical extension, and a second multi-color light source, the first and second multi-color light sources each casting light onto the light-reflecting surface, the light reflecting off the light-reflecting surface; and
    a filter coupled to the vertical extension and the base portion, at least a portion of the light reflected from the light reflecting surface passing through the filter,
    wherein the light-reflecting surface comprises a wall fixed relative to the base portion and the vertical extension, the apparatus further including a speaker disposed on a first side of the wall, wherein the light-reflecting surface is disposed on a second side of the wall, and wherein the second side is on an opposite side of the wall as the first side.

13. The apparatus of claim 12, wherein the filter includes a plurality of perforations.

14. The apparatus of claim 12, wherein the light-reflecting surface includes a plurality of perforation, wherein the speaker is configured to direct sound through the perforations.

15. An apparatus for producing multi-color illumination, comprising:
    a housing including a wall, the wall including a curved surface fixed relative to the housing;
    a first multi-color light source coupled to and disposed near a first end of the apparatus and casting light onto the curved surface, the first multi-color light source changing colors in accordance with at least one of a plurality of modes;
    a second multi-color light source coupled to and disposed near a second end of the apparatus opposite the first end and casting light onto the surface; and a user interface coupled to the housing and configured to control the at least one mode.

16. The apparatus of claim 15, further including a speaker attached to the wall at a side of the wall opposite the curved surface, the speaker configured to direct sound through the curved surface in accordance with the at least one mode.

17. The apparatus of claim 15, further including a speaker, wherein the speaker is attached to a first side of the wall, wherein the curved surface is a surface of a second side of the wall, and wherein the second side is on an opposite side of the wall as the first side.

18. The apparatus of claim 15, wherein the user interface includes a switch.

* * * * *